United States Patent
Govari et al.

(10) Patent No.: US 10,594,946 B2
(45) Date of Patent: Mar. 17, 2020

(54) OTOSCOPE WITH CONTROLLED ILLUMINATION

(71) Applicant: Biosense Webster (Israel) Ltd., Yokneam (IL)

(72) Inventors: Assaf Govari, Haifa (IL); Yaron Ephrath, Karkur (IL); Vadim Gliner, Haifa (IL); Christopher T. Beeckler, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 14/988,939

(22) Filed: Jan. 6, 2016

(65) Prior Publication Data

US 2016/0255261 A1    Sep. 1, 2016

Related U.S. Application Data

(60) Provisional application No. 62/126,112, filed on Feb. 27, 2015.

(51) Int. Cl.
| | |
|---|---|
| *H04N 5/235* | (2006.01) |
| *A61B 1/06* | (2006.01) |
| *A61B 1/04* | (2006.01) |
| *A61B 1/00* | (2006.01) |
| *H04N 5/225* | (2006.01) |

(Continued)

(52) U.S. Cl.
CPC ....... *H04N 5/2354* (2013.01); *A61B 1/00006* (2013.01); *A61B 1/04* (2013.01); *A61B 1/05* (2013.01); *A61B 1/06* (2013.01); *A61B 1/0607* (2013.01); *A61B 1/227* (2013.01); *H04N 5/2256* (2013.01); *H04N 5/2257* (2013.01); *A61B 1/00045* (2013.01); *A61B 1/00057* (2013.01); *H04N 2005/2255* (2013.01)

(58) Field of Classification Search
None
See application file for complete search history.

(56) References Cited

U.S. PATENT DOCUMENTS

| | | |
|---|---|---|
| 2002/0161280 A1 | 10/2002 | Chatenever et al. |
| 2003/0164952 A1 | 9/2003 | Deichmann et al. |

(Continued)

FOREIGN PATENT DOCUMENTS

| | | |
|---|---|---|
| JP | S60-85728 A | 5/1985 |
| JP | 2003-116783 A | 4/2003 |

(Continued)

OTHER PUBLICATIONS

European Search Report dated Jul. 14, 2017, International Application No. EP 16 15 7702.

(Continued)

*Primary Examiner* — Frederick D Bailey
(74) *Attorney, Agent, or Firm* — Frost Brown Todd LLC

(57) ABSTRACT

Apparatus, including a camera which has an objective lens configured to focus light from an object, and an imaging array configured to receive the focused light and in response thereto, to output a signal representative of an image of the object. The apparatus further includes a multiplicity of illuminators arrayed around the objective lens and configured to illuminate the object, and a processor which is coupled to differentially adjust respective light intensities emitted by the illuminators responsively to the signal.

19 Claims, 6 Drawing Sheets

(51) Int. Cl.
*A61B 1/227* (2006.01)
*A61B 1/05* (2006.01)

(56) References Cited

U.S. PATENT DOCUMENTS

| | | |
|---|---|---|
| 2006/0282009 A1 | 12/2006 | Oberg et al. |
| 2011/0077465 A1 | 3/2011 | Mizuyoshi et al. |
| 2012/0041267 A1 | 2/2012 | Benning et al. |
| 2012/0188402 A1* | 7/2012 | Guo ............... H04N 5/2351 348/223.1 |
| 2013/0033620 A1* | 2/2013 | Polidor ............ H04N 17/002 348/240.3 |
| 2013/0109959 A1* | 5/2013 | Baumgart ............ A61B 8/12 600/424 |
| 2013/0128223 A1* | 5/2013 | Wood ............ A61B 1/00034 351/206 |
| 2014/0037179 A1* | 2/2014 | Shida ............... A61B 5/0033 382/132 |
| 2015/0091447 A1* | 4/2015 | Kubo ............... A61B 1/045 315/153 |
| 2015/0109509 A1* | 4/2015 | Di Federico ........... G01C 11/00 348/333.02 |
| 2015/0351616 A1* | 12/2015 | Ruppersberg ...... A61B 1/00179 600/200 |

FOREIGN PATENT DOCUMENTS

| | | |
|---|---|---|
| JP | 2008-048905 A | 3/2008 |
| JP | 2013-235114 A | 11/2013 |
| JP | 2014-230708 A | 12/2014 |
| WO | WO 2014/184274 A1 | 11/2014 |

OTHER PUBLICATIONS

European Communication dated Jun. 30, 2017 for Application No. 16157702.8, 4 pages.
Chinese Office Action dated Nov. 21, 2018 for Application No. 201610108509.7, 13 pages.
Australian Office Action dated Aug. 28, 2019 for Application No. 2016200565, 3 pages.
Japanese Notification of Reasons for Refusal dated Dec. 20, 2019 for Application No. 2016-035410, 9 pages.

* cited by examiner

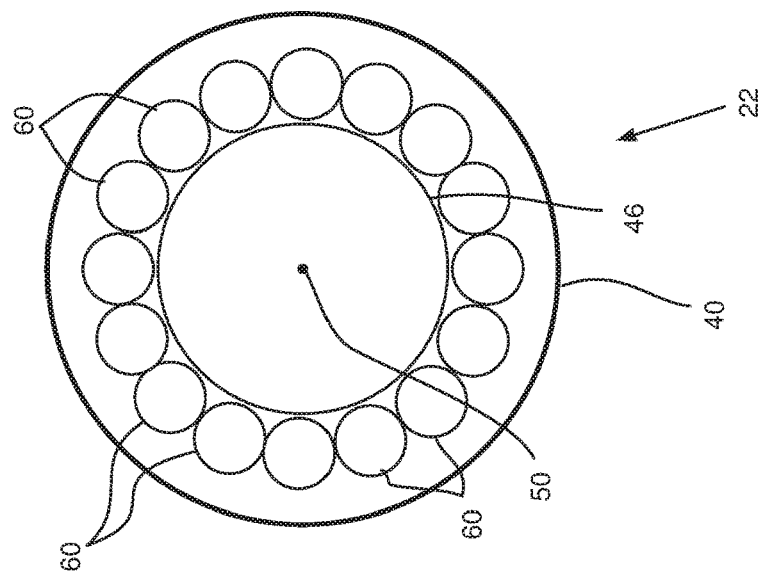
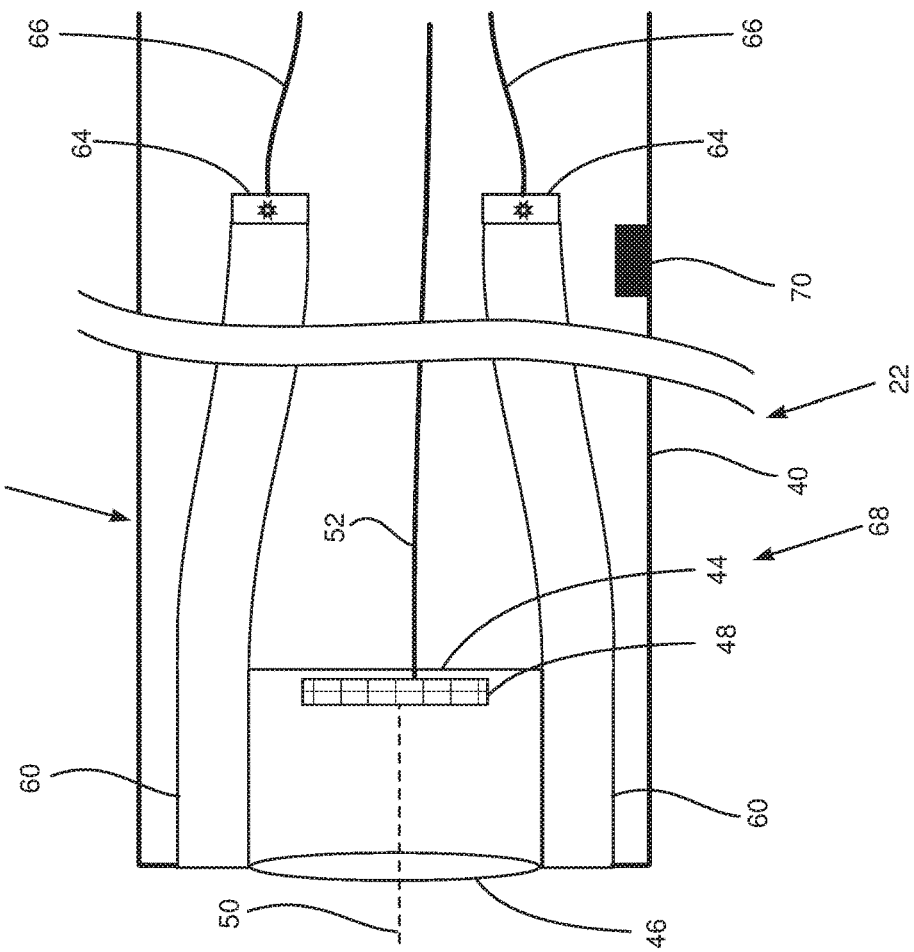

OTOSCOPE WITH CONTROLLED ILLUMINATION

FIELD OF THE INVENTION

The present invention relates generally to medical visual inspection equipment, and specifically to controlling the illumination used for such equipment.

BACKGROUND OF THE INVENTION

An endoscope, such as an otoscope, requires a light source in order to operate. A number of different combinations of endoscope and light source are known in the art.

U.S. patent application Ser. No. 12/892,697, entitled "Medical Apparatus and Endoscope Apparatus," filed on Sep. 28, 2010, published as U.S. Pub. No. 2011/0077465 on Mar. 31, 2011, now abandoned, to Mizuyoshi et al., whose disclosure is incorporated herein by reference, describes medical apparatus that includes an insertion unit and a light source which supplies light into the insertion unit. A surface of the insertion unit includes a first and second irradiation portions, wherein each of the first and second irradiation portions has a pair of irradiation windows which emits the light.

U.S. patent application Ser. No. 10/560,410, entitled "Device for Measuring Physical Properties of the Tympanic Membrane," filed on May 18, 2006, published as U.S. Pub. No. 2006/0282009 on Dec. 14, 2006, now abandoned, to Oberg et al., whose disclosure is incorporated herein by reference, describes a device for measuring physical properties of the tympanic membrane. The disclosure states that a device includes a first set of illumination fibres, and that each of the said illumination fibres is connected in a first end to one of a plurality of individually controllable light sources.

U.S. patent application Ser. No. 13/673,822, entitled "Digital-Based Medical Devices," filed Nov. 9, 2012, published as U.S. Pub. No. 2013/0128223 on May 23, 2013, issued as U.S. Pat. No. 8,944,596 on Feb. 3, 2015, to Wood et al., whose disclosure is incorporated herein by reference, describes a hand held ophthalmic examination instrument that uses an illumination system that provides amber colored light from a first light source and white light from a second light source to illuminate a target of interest. An imaging system in cooperation with the illumination system captures digital images of the target of interest as illuminated by the light sources.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:
a camera, consisting of:
an objective lens configured to focus light from an object; and
an imaging array configured to receive the focused light and in response thereto, to output a signal representative of an image of the object;
a multiplicity of illuminators arrayed around the objective lens and configured to illuminate the object; and
a processor, coupled to differentially adjust respective light intensities emitted by the illuminators responsively to the signal.

Typically, the object encompasses an area, and each of the illuminators is configured to only illuminate a respective partial section of the area. The respective partial section may be symmetric. Alternatively, the respective partial section may be asymmetric.

In a disclosed embodiment the processor is coupled to differentially adjust the respective light intensities so that a variation of an intensity of the focused light received by the array is within a preset range.

In a further disclosed embodiment, prior to the processor differentially adjusting the respective light intensities emitted by the illuminators, the processor records calibration data for the multiplicity of illuminators illuminating a calibration object, and applies the calibration data in adjusting the respective light intensities emitted by the illuminators responsively to the signal.

In a yet further disclosed embodiment the illuminators are configured to emit white light.

In an alternative embodiment the apparatus includes an orientation sensor providing a sensing signal indicative of an orientation of the camera, and the processor is configured to maintain the image presented on a screen in a fixed alignment responsively to the sensing signal.

The apparatus may include an otoscope.

In a further alternative embodiment the processor is coupled to adjust respective colors emitted by the illuminators responsively to the signal. The processor may be coupled to adjust the respective colors so that a color variation of the focused light received by the array is within a preset range.

There is further provided, according to an embodiment of the present invention, a method, including:
configuring an objective lens to focus light from an object;
configuring an imaging array to receive the focused light and in response thereto, to output a signal representative of an image of the object;
arraying a multiplicity of illuminators around the objective lens and configuring the illuminators to illuminate the object; and
differentially adjusting respective light intensities emitted by the illuminators responsively to the signal.

The present disclosure will be more fully understood from the following detailed description of the embodiments thereof, taken together with the drawings, in which:

BRIEF DESCRIPTION OF THE DRAWINGS

FIGS. 2A and 2B are respectively a schematic cross-section and a schematic front view of a distal portion of an otoscope, according to an embodiment of the present invention;

DETAILED DESCRIPTION OF EMBODIMENTS

Overview

An embodiment of the present invention provides a system which automatically adjusts the level of illumination provided by multiple illuminators used in endoscopic equipment, such as an otoscope. By providing such automatic adjustment, the system is able to compensate for variations in brightness of an object being viewed by the equipment. Each illuminator typically comprises a light emitter radiating into a respective fiber optic.

The multiple illuminators are arrayed around the objective lens of a camera, and the objective lens is configured to focus light from a viewed object onto an imaging array, typically a rectangular array of light-sensitive pixels. The array outputs a signal representative of an image of the object, and a processor is coupled to receive the signal. The processor uses the signal to differentially adjust respective light intensities emitted by the illuminators, typically so as to uniformly illuminate the object.

In some embodiments each of the illuminators is configured to only illuminate a respective partial section of the object, and the partial sections are arranged to be different for each illuminator. Such an arrangement enables the processor to adjust the light intensities from the different illuminators so as to vary a local illumination on the object, typically so that the object appears more uniformly bright.

In some embodiments the illuminators are configured to only emit white light. In alternative embodiments the illuminators are configured to emit white or colored light, and the color emitted by the illuminator may be varied. In the alternative embodiments a local illumination intensity on the object, as well as a local color illuminating the object, can be adjusted. Typically adjustments in the local color illumination may be used to correct for major color imbalances apparent in the object.

System Description

Figure 1:
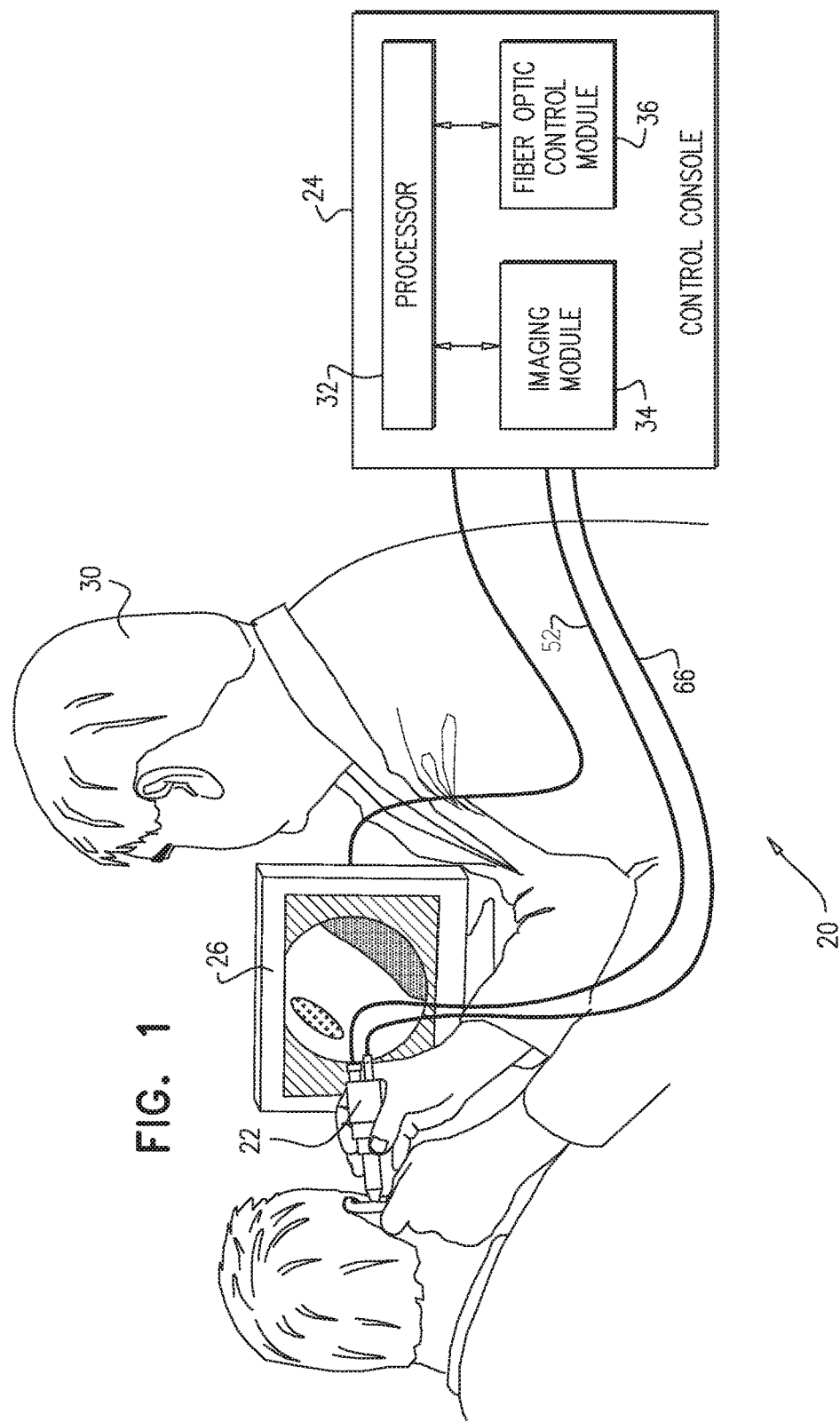
FIG. 1 is a schematic diagram illustrating operation of an otoscope system, according to an embodiment of the present invention.

Reference is now made to FIG. 1, which is a schematic diagram illustrating operation of an otoscope system 20, according to an embodiment of the present invention. By way of example, in the following description an otoscope 22 within system 20 is assumed to be controlled by a separate control console 24, and images from the otoscope are assumed to be presented on a separate screen 26. However it will be understood that one or more of console 24 and screen 26 may be combined with otoscope 22, for example as a single stand-alone instrument, and those having ordinary skill in the art will be able to adapt the description, mutatis mutandis, for these cases. It will also be understood that while otoscope system 20 is typically used for imaging within an ear, it may be used for imaging other orifices, such as the throat or nasal passages.

An operator 30, typically a medical professional, operates the otoscope system, and has overall control of console 24. The console comprises a central processor 32, which uses an imaging module 34 and a fiber optic control module 36 to perform functions necessary for operation of the otoscope system. The functions of the two modules are described in more detail below. Console 22 typically comprises other elements, such as a keypad or pointing device allowing operator 30 to communicate with processor 32 and the modules, as well as a memory for storage of software controlling the otoscope operation, but for simplicity such other elements are not illustrated in the figure. The controlling software may be downloaded to processor 32 in electronic form, over a network, for example, or it may, alternatively or additionally, be provided and/or stored on non-transitory tangible media, such as a magnetic, optical, or electronic memory.

FIGS. 2A and 2B are respectively a schematic cross-section and a schematic front view of a distal portion of otoscope 22, according to an embodiment of the present invention. A casing 40 retains elements of otoscope 22, which includes a camera 44. Camera 44 comprises an objective lens 46, at the distal end of the otoscope, together with an imaging array 48 which is configured to receive an image of an object such as an eardrum of an ear. Objective 46 and array 48 are orthogonal to, and define, an optic axis 50 of the camera. The image is focused onto array 48 by the objective lens, and the array, typically a charge coupled device (CCD) or a CMOS (complementary metal oxide semiconductor) device, comprises a rectangular array of light-sensitive pixels. A cable 52 connects array 48 to imaging module 34, enabling the module to provide driving signals to the array, as well as to receive electrical signals generated by the array in response to its received images. The images received by module 34 may be displayed on screen 26.

Surrounding objective 46 and camera 44 are a multiplicity of substantially similar fiber optics 60, which terminate at the distal end of the otoscope at approximately the same plane of casing 40 containing the objective lens. Typically, although not necessarily, the fiber optics are in one layer and are distributed symmetrically about axis 50. In some embodiments the fiber optics in the one layer may be close packed. By way of example, FIG. 2B illustrates 16 close packed fiber optics 60 in one layer around the objective lens. The fiber optics terminate at approximately the same plane as the objective lens, as shown in FIG. 2A.

Each fiber optic is configured to provide illumination that partially spatially covers the object being imaged by array 48, and the illumination from each fiber optic is individually controllable. Thus, at a proximal end of each fiber optic 60 there is a respective light emitter 64, typically a light emitting diode (LED), which is coupled by a respective cable 66, typically bundled into a single cable, to fiber optic control module 36. Each fiber optic 60 may be configured so that its proximal end is within casing 40. Alternatively, the proximal end may be configured to be in another location, such as within control console 26.

In some embodiments the light emitted from each emitter 64 is assumed to be white light. In alternative embodiments the light emitted from each emitter may be white or colored. In all embodiments the intensity of the illumination emitted by each light emitter 64 is controlled by module 36, and the module is also able to switch each light emitter on or off. For embodiments where the emitter color is variable, module 36 is able to control the color of the individual emitters, typically by adjusting a red, green, and/or blue component of the emitted light. Each pair of fiber optic 60 and light emitter 64 is also referred to herein as an illuminator 68.

In some embodiments otoscope 22 comprises an orientation sensor 70, which is configured to provide a sensing signal indicative of an orientation of camera 44 to processor 32. The function of the orientation sensor is described further below.

Figure 3:
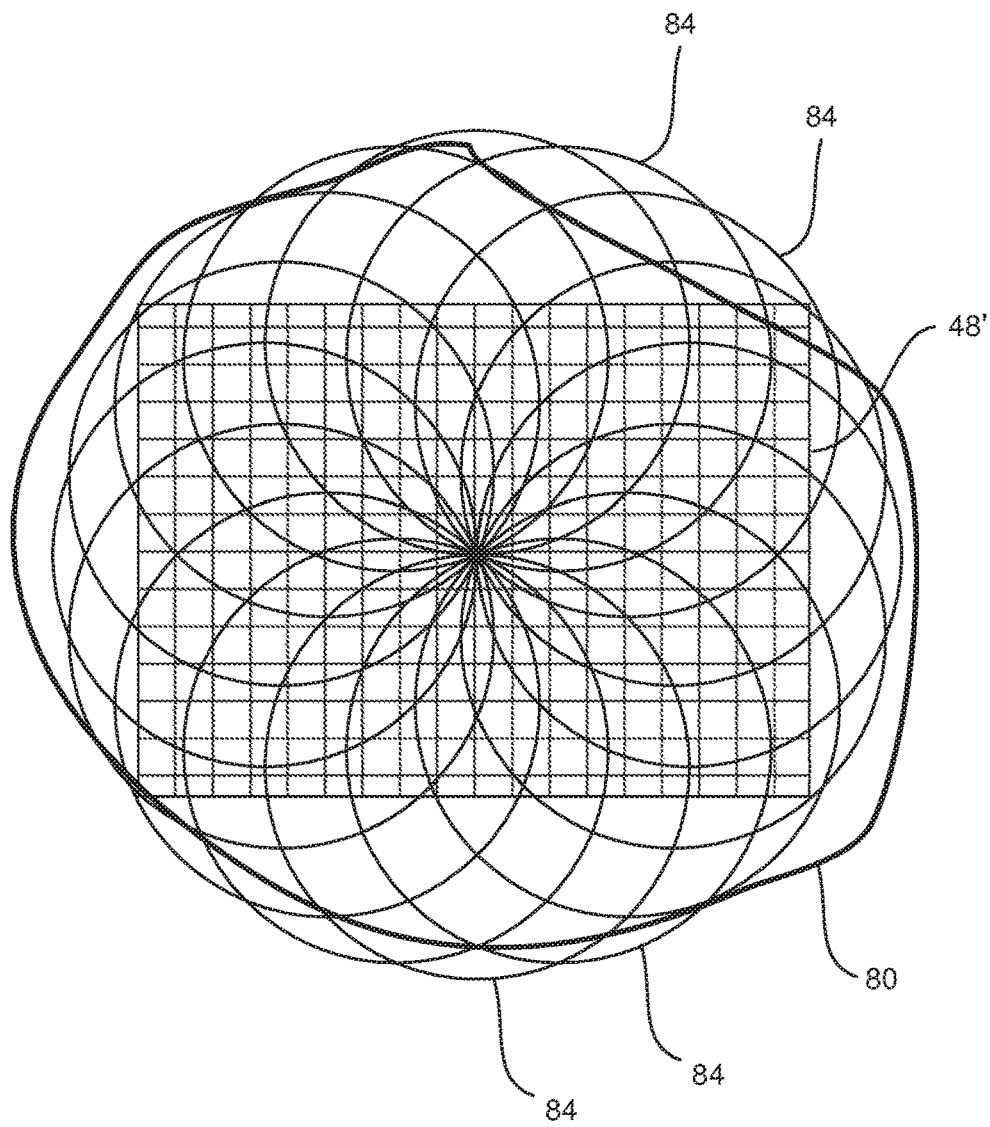
FIG. 3 is a schematic diagram illustrating how an object is illuminated by fiber optics, according to an embodiment of the present invention.

FIG. 3 is a schematic diagram illustrating how an object 80 is illuminated by illuminators 68, according to an embodiment of the present invention. Illuminated object 80 is assumed to be approximately plane, in the plane of the paper. As stated above, the illuminated object is imaged by lens 46 at array 48, so that object 80 and the array 48 are at conjugate points of the lens. The figure shows array 48 projected to its corresponding conjugate point, at the object, as a rectangle 48', so that the diagram can also be considered as representing how the different illuminated portions of object 80 are imaged at array 48.

The illumination from each fiber optic of an illuminator projects approximately as a cone, intersecting the plane of the paper as a circle. As shown in the diagram, a given circle from a specific fiber optic only illuminates a partial area of the object. By way of example, object 80 may be assumed to comprise the eardrum, having an approximate diameter of 10 mm, and rectangle 48' may be assumed to have dimensions of 8 mm×6 mm, and a diagonal of 10 mm, for a typical CCD array 48 having a dimensional ratio of 4:3. The circles of illumination projected at object 80 are assumed to have diameters of approximately 5 mm. For the example described above, of 16 fiber optics surrounding the objective lens, there are a corresponding 16 circles 84 of approximate diameters 5 mm each, and the circles are assumed to be arranged symmetrically about the center of rectangle 48', i.e., about axis 50.

The numerical values provided above are purely by way of example, and it will be understood that embodiments of the present invention are in no way limited by these exemplary numbers. Thus, embodiments of the present invention may have any convenient number of fiber optics surrounding the objective lens, and the light projected from each of the fiber optics may have different dimensions than the circular diameter given above, while each circle still only provides partial coverage of the illuminated object. In addition, rather than the light projecting as a circle, it may project as another figure, which may have some symmetry, such as being elliptical or oval, or which may have no symmetry, being a completely asymmetric figure. Furthermore, there is no requirement that the fiber optics, or that the light from them, be distributed in a symmetric manner. As will be apparent from the flowchart of FIG. 4 described below, these and other points are accounted for in calibration of otoscope 22.

Figure 4:
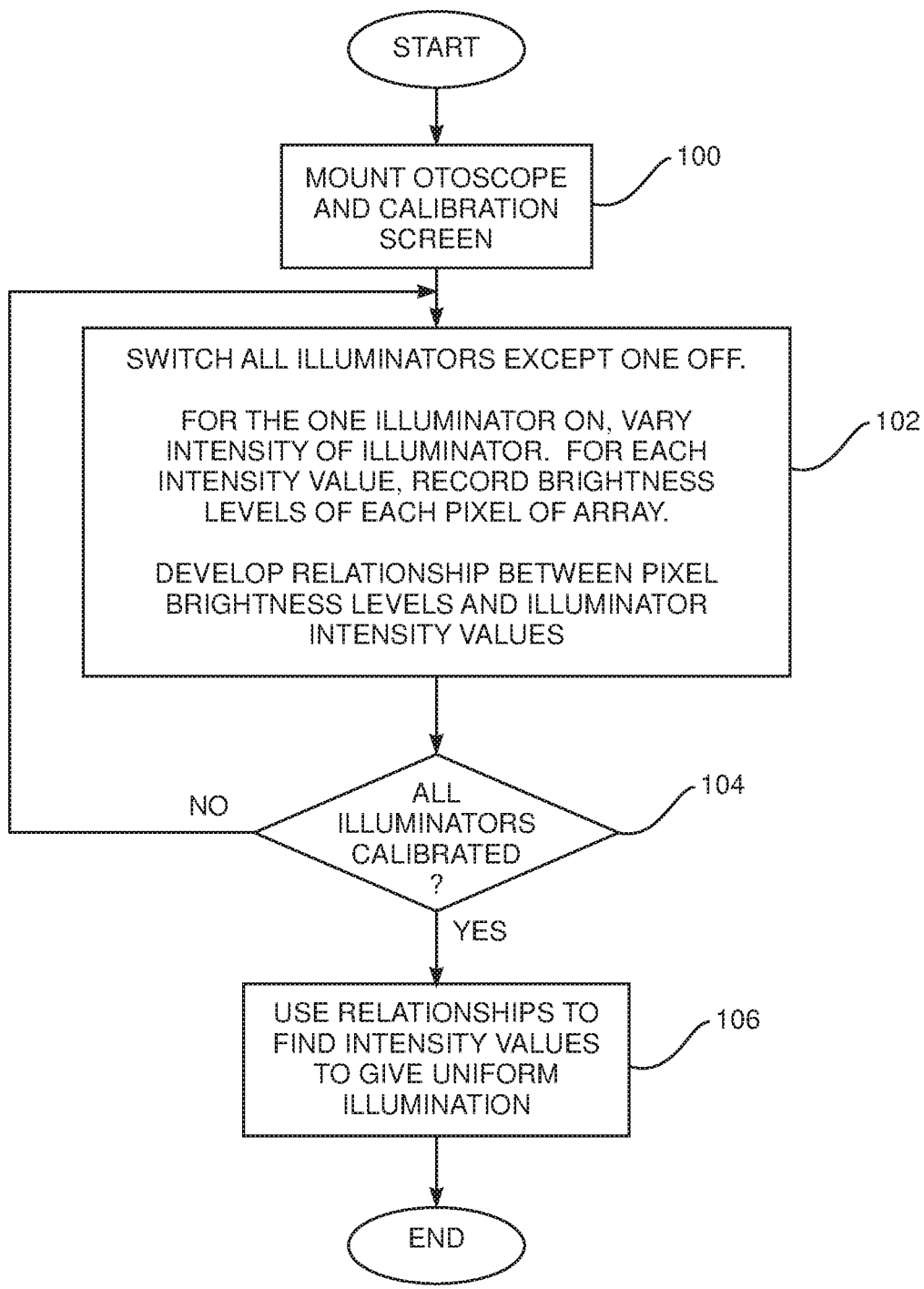
FIG. 4 is a flowchart of steps for calibrating an otoscope, according to an embodiment of the present invention.

FIG. 4 is a flowchart of steps for calibrating otoscope 22, according to an embodiment of the present invention. The calibration process maps the illumination from each illuminator 68 on a calibration object, herein assumed to be a white screen, as it is imaged by array 48.

In a setup step 100, otoscope 22 is mounted so that the white screen is at a predetermined distance from the distal end of the otoscope, and is orthogonal to axis 50. Typically, the predetermined distance is based on an intended use of the otoscope, so that if the otoscope is to be used to examine the eardrum, the distance is somewhat less than the length of the auditory canal, i.e., about 20 mm. In this calibration process, emitters 64, for all embodiments, are set to give only white light.

In a calibration step 102, fiber optic control module 36 switches off all emitters 64 of illuminators 68, except one. For the one illuminator that is operational, the module changes values of the light intensity it emits, typically by applying different potentials to the light emitter.

For each potential applied to the single "on" emitter, i.e., for each respective value of the light intensity I from the illuminator, array 46 acquires an image of the screen, and module 36 records the value of the brightness level L at each pixel (x, y) of the array. Based on the recorded values, processor 32 and module 36 develops a relationship, herein assumed to comprise a matrix [M], relating brightness levels for each pixel for different intensities I, according to equation (1):

$$[(x,y,L)] = [M] \cdot [I] \tag{1}$$

Equation (1) represents a calibration equation for the selected illuminator 68 and its corresponding fiber optic.

As shown by a condition step 104, processor 32 and module 36 repeat the calibration for each illuminator 68, comprising a fiber optic and its coupled light emitter, in the otoscope. The iteration produces sets of equations (2), so that for each emitter/fiber optic combination, processor 32 develops and records a matrix [M].

$$[(x,y,L)]_n = [M]_n \cdot [I]_n \tag{2}$$

where n is an identifier of a given emitter/fiber optic combination.

Once the iterations of step 104 have completed, the flowchart continues to a final uniform illumination step 106. In step 106, processor 32 analyzes the matrices $[M]_n$, and sets the potentials of each emitter so that the overall illumination provided is uniform. That is, so that the overall variation of the levels produced on array 46, i.e., the variation in the brightness values of the array pixels, when illuminators 68 are illuminating the white calibration screen, is within a preset range of brightness levels, for a given mean brightness level. If necessary, the processor adjusts the potentials of each emitter to accord with the preset range of brightness levels. The variation may be measured by any means known in the art, such as by the variance of the brightness values, or by a difference between a maximum brightness value and a minimum brightness value.

The analysis results in the processor finding and recording settings for the potential applied, separately and individually, to each emitter 64, for the given mean brightness level. The processor may repeat the finding of emitter settings for different mean brightness levels. Alternatively or additionally, the processor may use the settings found for the given mean brightness level to estimate settings for other mean brightness levels.

Review of the calibration process flowchart indicates that the calibration accommodates substantially any arrangement of fiber optics 60, as well as substantially any arrangement of the figures projected by the fiber optics, since the calibration process maps respective illumination regions of each emitter 64.

Figure 5:
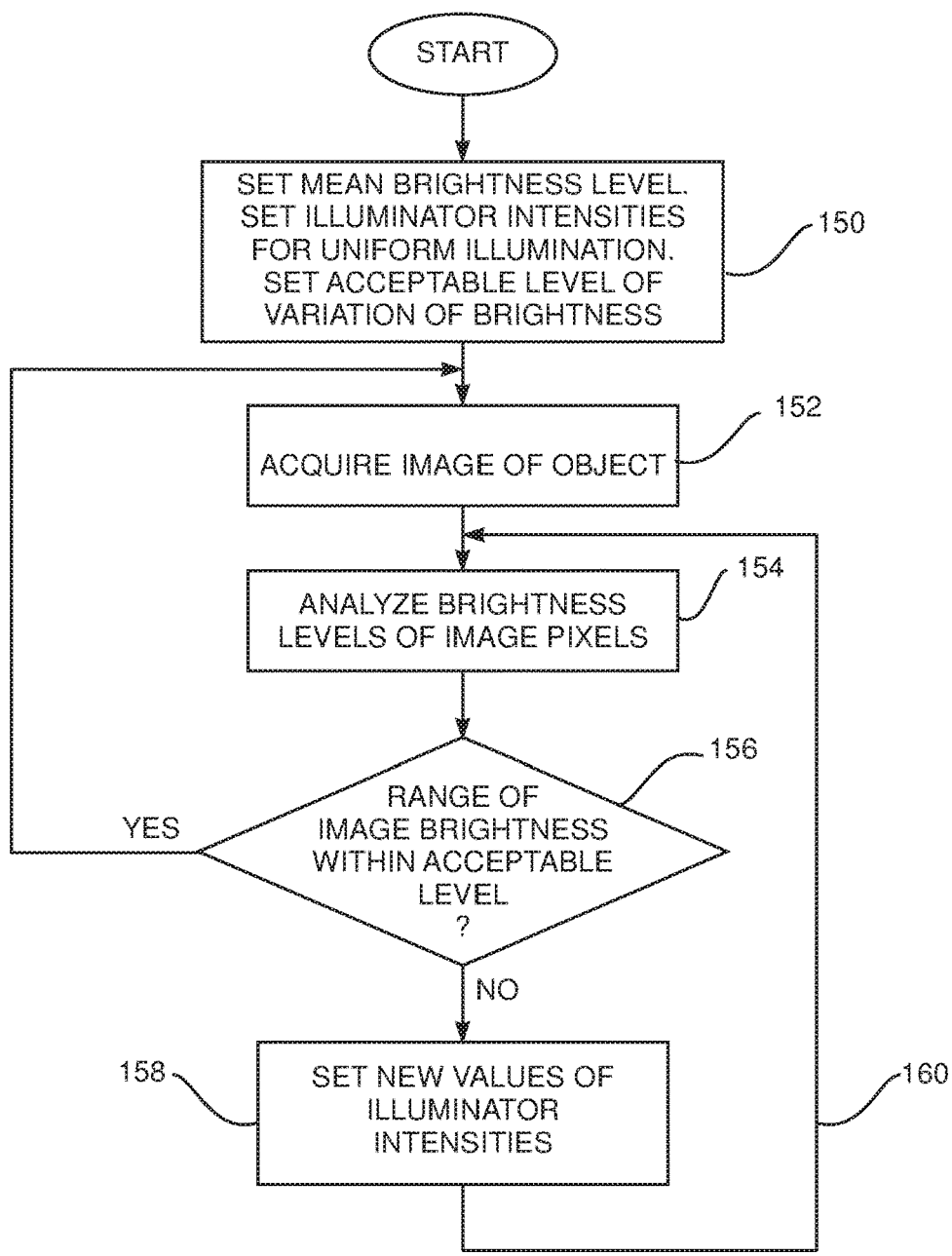
FIG. 5 is a flowchart of steps for operating an otoscope in the system of FIG. 1, according to an embodiment of the present invention.

FIG. 5 is a flowchart of steps for operating otoscope 22 in system 20, according to an embodiment of the present invention. The flowchart applies the calibration matrices for each of the emitter/fiber optic combinations derived by the calibration process of FIG. 4. The flowchart assumes that the emitters of the otoscope are configured to only emit white light.

In a setup step 150, operator 30 inserts otoscope 22 into an ear. Typically, prior to the insertion, processor 32 initially sets the intensity level of each emitter 64 according to the potential values determined in step 106 of the calibration flowchart, i.e., so that the overall illumination is uniform, for a mean brightness level that is selected by operator 30. In addition, operator 30 may set an acceptable level of variation of the brightness of an image. Such an acceptable level is typically different from the preset range of brightness values used for calibration of the otoscope, because of expected structure in the object being imaged. The acceptable level of variation may be determined, for example, on the basis of an expected object to be imaged. Alternatively, the accepted level of variation may be determined by the operator by other means, such as using results from previous imaging by the otoscope, without undue experimentation.

In an operational step 152, after insertion of the otoscope, array 46 acquires an image of the object being illuminated. It will be understood that because the object typically has structure, and so is different from the substantially uniform white screen used in the calibration process, the variation of brightness levels of the pixels of the acquired image is typically different from the preset range used for step 106 of the calibration process.

In an analysis step 154, the processor analyzes the brightness level of the pixels of the acquired image. If, in a decision step 156 the range of levels is within the acceptable level set in step 150, no action is taken, and the flowchart returns to step 152 to acquire another image. If decision step 156 returns that the range of levels is outside the acceptable level, then in an adjustment step 158 the processor differentially adjusts the intensities of the illuminators. To implement the differential adjustment, the processor uses the matrices recorded in the calibration process of FIG. 4 to determine new intensities to be provided by illuminators 68, while maintaining the mean brightness level selected by the operator in step 150. The processor then separately and differentially adjusts the potentials applied to the illuminators accordingly. As indicated by the arrow 160, steps 158, 154, and 156 may be performed iteratively.

For example, if the left side of the acquired image is dim and distant, while the right side is bright and near, the processor increases the intensities provided by illuminators 68 illuminating the left side of the object, while decreasing the intensities provided by illuminators illuminating the right side of the object. The processor changes the intensities so as to maintain the selected mean brightness level.

The images generated in implementation of the flowchart are presented on screen 26. In embodiments comprising orientation sensor 70 (FIG. 1), processor 32 may use the sensing signal provided by the sensor to fix the alignment of the image on screen 26, regardless of the orientation of otoscope 22.

Figure 6:
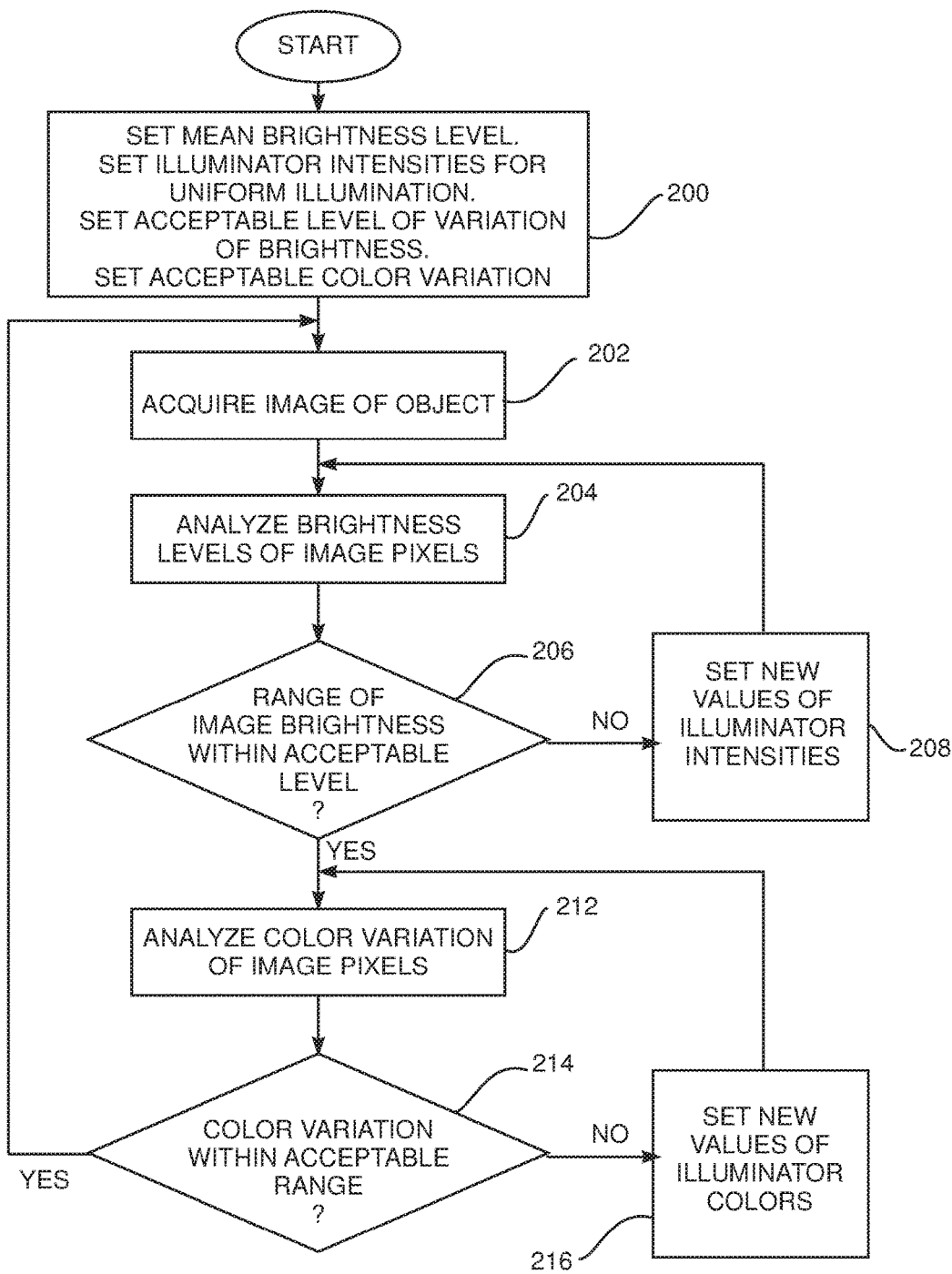
FIG. 6 is a flowchart of steps for operating an otoscope in the system of FIG. 1, according to an alternative embodiment of the present invention.

FIG. 6 is a flowchart of steps for operating otoscope 22 in system 20, according to an alternative embodiment of the present invention. The flowchart assumes that the emitters of the otoscope are configured to emit white or colored light. As for the flowchart of FIG. 5, the flowchart of FIG. 6 applies the calibration matrices for each of the emitter/fiber optic combinations derived by the calibration process of FIG. 4.

A setup step 200 is substantially as described above for setup step 150, except that in addition operator 30 may set an acceptable level of variation of the color of an image. The acceptable level of color variation may be determined, for example, on the basis of an expected object to be imaged. Alternatively, the accepted level of color variation may be determined by the operator by other means, such as using results from previous imaging by the otoscope, without undue experimentation.

In setup step 200, prior to insertion of the otoscope, processor 32 initially sets each emitter 64 to emit white light, and sets the intensity level of each emitter 64 according to the potential values determined in step 106 of the calibration flowchart, i.e., so that the overall illumination is uniform, for a mean brightness level that is selected by operator 30.

Steps 202, 204, 206, and 208 are substantially as described above respectively for steps 152, 154, 156, and 158 of the flowchart of FIG. 5. However, if step 206 returns a positive value, so that the image brightness variation is within an acceptable range, a further set of steps, beginning with an analysis step 212, are invoked to check a color variation of the acquired image.

In analysis step 212, the processor analyzes the color variation of the pixels of the acquired image. If, in a decision step 214 the variation is within the acceptable level set in step 200, no action is taken, and the flowchart returns to step 202 to acquire another image.

If decision step 214 returns that the range of levels is outside the acceptable level, then in an adjustment step 216 the processor adjusts the color of the illuminators. To implement the color adjustment, the processor analyzes the color values of the array pixels, typically on a local basis corresponding to the mapped region of emitters 64 determined in the calibration process of FIG. 4. From the analysis, the processor may decide to increase, decrease, or leave unaltered the color transmitted by a given emitter 64. The process of the flowchart then returns, on an iterative basis, to step 212.

For example, if the left side of the array has a strong red element, typically caused by an effusion of blood, then the processor may reduce the red values of emitters 64 effectively transmitting to the left side of the array. The processor may also increase the red values of emitters 64 effectively transmitting to the right side of the array. Other types of adjustment to compensate for the color levels being outside the acceptable level, as returned by decision step 214, will be apparent to those having ordinary skill in the art, and all such adjustments are included within the scope of the present invention.

While the description hereinabove refers generally to an otoscope, it will be understood that the scope of the present invention applies to other endoscopic equipment, such as a rhinoscope or a colonoscope.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus, comprising:
   (a) a camera, comprising:
      (i) an objective lens configured to focus light from an object, and
      (ii) an imaging array configured to receive the focused light and in response thereto, to output a signal representative of an image of the object;
   (b) a multiplicity of illuminators arrayed around the objective lens and configured to illuminate the object, wherein the illuminators are positioned in an annularly arranged array about the objective lens, wherein the illuminators distally terminate at respective distal ends that are substantially coplanar with the objective lens; and
   (c) a processor configured to:
      (i) perform a calibration process to determine and set an intensity value for each of the multiplicity of illuminators, wherein the intensity values are configured to cause the multiplicity of illuminators to provide uniform illumination when directed at a calibration object, and (ii) after performing the calibration process, perform an imaging process to capture images with the imaging array while adjusting the intensity of each of the multiplicity of illuminators in order to maintain uniform illumination, wherein the calibration object comprises a surface adapted to reflect light uniformly, wherein the object encompasses an area, and wherein each of the illuminators is configured to only illuminate a respective partial section of the area.

2. The apparatus according to claim 1, wherein the respective partial section is symmetric.

3. The apparatus according to claim 1, wherein the illuminators are configured to emit white light.

4. The apparatus according to claim 1, further comprising an orientation sensor providing a sensing signal indicative of an orientation of the camera, and wherein the processor is configured to maintain the image presented on a screen in a fixed alignment responsively to the sensing signal.

5. The apparatus according to claim 1, wherein the apparatus comprises an otoscope.

6. The apparatus of claim 1, wherein the processor is further configured to, when performing the calibration process, and for each illuminator in the multiplicity of illuminators:

(i) enable that illuminator at a first intensity while disabling all others and capture an image of the calibration object with the imaging array, (ii) determine a brightness value of each pixel of the image to produce a brightness map that indicates a relationship between pixel brightness of each pixel of the image and the first intensity, and (iii) vary the intensity at which that illuminator is enabled to a set of subsequent intensities and produce a set of brightness maps for each of the set of subsequent intensities, and wherein the processor is further configured to set the intensity for each illuminator of the multiplicity of illuminators based upon the set of brightness maps such that the variation in brightness values is within a preset range.

7. The apparatus of claim 1, wherein the processor is further configured to, when performing the calibration process, produce a set of brightness maps that indicate a relationship between brightness of each pixel of the imaging array and intensities of each of the multiplicity of illuminators, and wherein the processor is further configured to, when performing the imaging process:

(i) capture an image with the imaging array and determine a brightness value of each pixel of the image to produce a range of brightness, and (ii) where the range of brightness is not within an acceptable range, differentially adjust the intensities of one or more of the multiplicity of illuminators using the brightness map until the range of brightness is within the acceptable range.

8. The apparatus of claim 7, wherein the acceptable range is determined as a preset range, a user defined range, or a combination of the preset range and the user defined range.

9. The apparatus of claim 1, wherein the processor is further configured to, when performing the imaging process, perform a color balancing process to adjust the color of illumination provided by each of the multiplicity of illuminators in order to maintain the range of colors within an acceptable range.

10. The apparatus of claim 9, wherein the processor is further configured to, when performing the color balancing process:

(i) determine a color value for each pixel of a captured image to produce a range of color, wherein the captured image was captured during a previous step of the imaging process, and (ii) where the range of color is not within the acceptable range, adjust the color of illumination provided by one or more of the multiplicity of illuminators on a local basis.

11. The apparatus of claim 2, wherein the multiplicity of illuminators comprises a set of sixteen illuminators, wherein the multiplicity of illuminators are positioned symmetrically about the objective lens, and wherein each illuminator of the multiplicity of illuminators is in contact with two other illuminators of the multiplicity of illuminators.

12. A method, comprising:

(a) configuring an objective lens to focus light from an object;

(b) configuring an imaging array to receive the focused light and in response thereto, to output a signal representative of an image of the object;

(c) arraying a multiplicity of illuminators around the objective lens and configuring the illuminators to illuminate the object;

(d) performing a calibration process to determine and set an intensity value for each of the multiplicity of illuminators, wherein the intensity values are configured to cause the multiplicity of illuminators to provide uniform illumination when directed at a calibration object, and wherein the calibration object comprises a surface adapted to reflect light uniformly;

(e) after performing the calibration process, performing an imaging process to capture images with the imaging array while differentially adjusting respective light intensities emitted by the illuminators responsively to the signal in order to maintain uniform illumination;

(f) receiving a first image captured with the imaging array at a first orientation and rendering the first image at the first orientation;

(g) receiving a second image captured with the imaging array at a second orientation;

(h) sensing a change in orientation of the imaging array from the first orientation to the second orientation; and (i) in response to the sensed change in orientation, rendering the second image in the first orientation, thereby providing consistent alignment of the rendered image despite reorientation of the imaging array.

13. The method according to claim 12, wherein the respective partial section is symmetric.

14. The method according to claim 12, wherein the respective partial section is asymmetric.

15. The method according to claim 12, further comprising, when performing the imaging process, differentially adjusting the respective light intensities so that a variation of an intensity of the focused light received by the array is within a preset range in order to maintain uniform illumination.

16. The method according to claim 12, further comprising, when performing the calibration process, recording calibration data for the multiplicity of illuminators illuminating the calibration object, wherein the calibration object is a white screen.

17. The method according to claim 12, wherein the illuminators are configured to emit white light.

18. The method according to claim 12, further comprising adjusting respective colors emitted by the illuminators responsively to the signal.

19. The method according to claim 18, further comprising adjusting the respective colors so that a color variation of the focused light received by the array is within a preset range.

* * * * *